US006852661B1

(12) United States Patent
Ahlers et al.

(10) Patent No.: US 6,852,661 B1
(45) Date of Patent: Feb. 8, 2005

(54) CATALYST COMPRISING A METAL COMPLEX OF THE VIII SUBGROUP BASED ON A PHOSPHINE AMIDITE LIGAND AND ITS UTILIZATION FOR HYDROFORMYLATION AND HYDROCYANATION

(75) Inventors: Wolfgang Ahlers, Worms (DE); Heiko Maas, Schifferstadt (DE); Michael Röper, Wachenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/937,310

(22) PCT Filed: Mar. 23, 2000

(86) PCT No.: PCT/EP00/02610

§ 371 (c)(1),
(2), (4) Date: Sep. 24, 2001

(87) PCT Pub. No.: WO00/56451

PCT Pub. Date: Sep. 28, 2000

(30) Foreign Application Priority Data

Mar. 24, 1999 (DE) .......................................... 199 13 352

(51) Int. Cl.[7] ........................ B01J 31/00; C07C 253/00; C07C 45/00; C07C 45/90
(52) U.S. Cl. ...................... 502/162; 502/167; 558/335; 558/338; 558/339; 558/340; 568/429; 568/454; 568/455; 568/456
(58) Field of Search ................................ 502/117, 162, 502/167; 558/335, 338, 339, 340; 568/429, 454, 455, 456

(56) References Cited

U.S. PATENT DOCUMENTS

| 4,169,861 A | 10/1979 | Hughes ...................... 260/604 |
| 5,312,996 A | 5/1994 | Packett ....................... 568/454 |
| 5,360,938 A | 11/1994 | Babin et al. ................. 568/449 |
| 5,710,344 A | 1/1998 | Breikss et al. .............. 568/454 |
| 5,874,639 A | 2/1999 | Nicholson et al. .......... 568/454 |

FOREIGN PATENT DOCUMENTS

| JP  | 09 255 610  | 9/1997  |
| WO  | WO 95/30680 | 11/1995 |
| WO  | WO 96/16923 | 6/1996  |

OTHER PUBLICATIONS van Rony et al. "Phophoramidites: a novel nodifying ligands in rhodium catalyzed hydroformylation" Recl. Trav. Chim Pays–Bas. No. 115 (1996) pp. 492–498.

Tolman et al. "Homogeneous Nickel–Catalyzed Olefin Hydrocyanation" Advances in Catalysts vol. 33 (1985) pp. 2–46.

Tolman et al. "Catalytic Hydrocyanation of Olefins by Nickel (0) Phosphite Complexes—Effects of Lewis Acids[†]" Organometallics vol. 3, (1984) pp. 33–38.

Huthmacher et al. "Reactions with Hydrogen and Cyanide (Hydrocyanation)" Applied Homogeneous Catalysts with Organometallic Compounds (1996) pp. 465–486.

Beller et al. "Progress in hydroformylation and carbonylation" Journal of Molecular Catalysts A vol. 104 (1995) pp. 17–85.

*Primary Examiner*—Mark L. Bell
*Assistant Examiner*—J. Pasterczyk
(74) *Attorney, Agent, or Firm*—Keil & Weinkauf

(57) ABSTRACT

A catalyst comprising at least one complex of a metal of transition group VIII comprising at least one monodentate, bidentate or multidentate phosphinamidite ligand in which the phosphorus atom and the oxygen atom of the phosphinamidite group form part of a 5- to 8-membered heterocycle can be used for the hydroformylation and hydrocyanation of compounds containing at least one ethylenically unsaturated double bond. The phosphinamidite ligand is, for example, represented by the following formulae

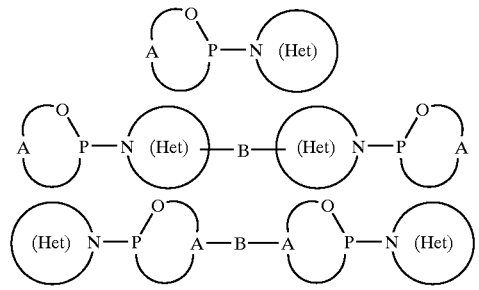

wherein

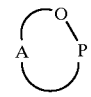

represents an optionally substituted 5- to 8-membered heterocycle wherein A represents carbon ring members;

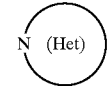

represents an optionally substituted N-bonded heterocycle wherein (Het) indicates optional ring heteroatoms in addition to the N; and B is a carbon-carbon single bond or a divalent bridging group.

10 Claims, No Drawings

CATALYST COMPRISING A METAL COMPLEX OF THE VIII SUBGROUP BASED ON A PHOSPHINE AMIDITE LIGAND AND ITS UTILIZATION FOR HYDROFORMYLATION AND HYDROCYANATION

The present invention relates to a catalyst comprising at least one complex of a metal of transition group VIII comprising at least one monodentate, bidentate or multidentate phosphinamidite ligand, and also processes for the hydroformylation and hydrocyanation of compounds containing at least one ethylenically unsaturated double bond in the presence of such a catalyst.

Hydroformylation, also known as the oxo process, is an important industrial process and is employed for the preparation of aldehydes from olefins, carbon monoxide and hydrogen. If desired, these aldehydes can be hydrogenated by means of hydrogen in the same process step to form the corresponding oxo alcohols. The reaction itself is strongly exothermic and generally proceeds under superatmospheric pressure at elevated temperatures in the presence of catalysts. Catalysts used are Co, Rh, Ir, Ru, Pd or Pt compounds or complexes which can be modified with N- or P-containing ligands to influence the activity and/or selectivity. Owing to the possible addition of CO onto each of the two carbon atoms of a double bond, the hydroformylation reaction forms mixtures of isomeric aldehydes. In addition, double bond isomerization can also occur. In these isomeric mixtures, the n-aldehyde is frequently formed preferentially compared to the iso-aldehyde, and, owing to the significantly greater industrial importance of the n-aldehydes, attempts are made to optimize the hydroformylation catalysts so as to achieve a greater n-selectivity.

Beller et al., Journal of Molecular Catalysis A, 104 (1995), pages 17–85, describes rhodium-containing, phosphine-modified catalysts for the hydroformylation of low-boiling olefins. Disadvantages of these catalysts are that they can only be prepared using organometallic reagents and that the ligands used are complicated and expensive to prepare. In addition, the hydroformylation of internal straight-chain and branched olefins and also of olefins having more than 7 carbon atoms is very slow when these phosphine-modified catalysts are used.

WO 95/30680 describes bidentate phosphine ligands in which the two phosphine groups are each bound to an aryl radical and these two aryl radicals form a doubly bridged, ortho-fused ring system in which one of the two bridges consists of an oxygen or sulfur atom. Rhodium complexes based on these ligands are suitable as hydroformylation catalysts, with a good n/iso ratio being achieved in the hydroformylation of terminal olefins. A disadvantage of these chelating phosphines is their complicated preparation, so that industrial processes based on such chelating phosphine catalysts have an economic disadvantage.

U.S. Pat. No. 4,169,861 describes a process for preparing terminal aldehydes by hydroformylation of $\alpha$-olefins in the presence of a rhodium hydroformylation catalyst based on one bidentate ligand and one monodentate ligand. As bidentate ligand, preference is given to using 1,1'-bis (diphenylphosphino)ferrocene. The monodentate ligand is preferably a phosphine such as diphenylethylphosphine. U.S. Pat. Nos. 4,201,714 and 4,193,943 make similar disclosures. The preparation of the bidentate phosphinoferrocene ligands requires the use of organometallic reactions which are complicated to prepare, as a result of which hydroformylation processes using these catalysts have an economic disadvantage.

U.S. Pat. No. 5,312,996 describes a process for preparing 1,6-hexanedial by hydroformylation of butadiene in the presence of hydrogen and carbon monoxide. Hydroformylation catalysts used are rhodium complexes having polyphosphite ligands in which the phosphorus and two of the oxygen atoms of the phosphite group are part of a 7-membered heterocycle.

JP-A 97/255 610 describes a process for preparing aldehydes by hydroformylation in the presence of rhodium catalysts which have a monodentate phosphonite ligand.

The catalytic hydrocyanation for producing nitriles from olefins is likewise of great industrial importance.

In "Applied Homogeneous Catalysis with Organometalic Compounds", Vol. 1, VCH Weinheim, p. 465 ff., the heterogeneously and homogeneously catalyzed addition of hydrogen cyanide onto olefins is described in general terms. Here, use is made, in particular, of catalysts based on phosphine, phosphite and phosphonite complexes of nickel and palladium.

In Organometallics 1984, 3, p. 33 ff., C. A. Tolman et al., describe the catalytic hydrocyanation of olefins in the presence of nickel(0)-phosphite complexes with special reference to the effects of Lewis acids on the hydrogen cyanide addition.

In Advances in Catalysis, Volume 33, 1985, Academic Press Inc., p. 1 ff., a review of the homogeneously nickel-catalyzed hydrocyanation of olefins is given. Catalysts used are nickel(0) complexes comprising phosphine and phosphite ligands.

None of the abovementioned literature references describes hydroformylation catalysts or hydrocyanation catalysts based on monodentate, bidentate or multidentate phosphinamidite ligands in which the phosphorus atom and the oxygen atom of the phosphinamidite group are part of a 5- to 8-membered heterocycle.

It is an object of the present invention to provide new catalysts based on complexes of a metal of transition group VIII. These should preferably be suitable for hydroformylation or hydrocyanation reactions and have a good catalytic activity.

We have found that this object is achieved by catalysts based on complexes of a metal of transition group VIII which comprise at least one monodentate, bidentate or multidentate phosphinamidite ligand in which the phosphorus atom and the oxygen atom of the phosphinamidite group are part of a 5- to 8-membered heterocycle.

The present invention accordingly provides a catalyst comprising at least one complex of a metal of transition group VIII comprising at least one monodentate, bidentate or multidentate phosphinamidite ligand of the formulae I.1, I.2 and/or I.3

(I.1)

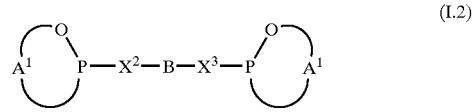

(I.2)

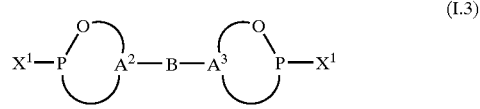

(I.3)

where $A^1$ together with the phosphorus atom and the oxygen atom to which it is bound form a 5- to 8-membered heterocycle onto which one, two or three cycloalkyl, aryl and/or hetaryl groups may be fused, where the fused-on groups may each bear, independently of one another, one, two or three substituents selected from among alkyl, alkoxy, halogen, nitro, cyano, carboxyl and carboxylate, $A^2$ and $A^3$ are, independently of one another, part of a heterocycle as defined for $A^1$ which is substituted by B, $X^1$ is a 5- to 8-membered heterocycle which contains at least one nitrogen atom bound directly to the phosphorus atom, where the heterocycle may additionally contain one or two heteroatom(s) selected from among N, O and S and/or one, two or three cycloalkyl, aryl and/or hetaryl groups may be fused onto the heterocycle, where the heterocycle and/or the fused-on groups may each bear, independently of one another, one, two or three substituents selected from among alkyl, cycloalkyl, aryl, alkoxy, cycloalkoxy, aryloxy, acyl, halogen, trifluoromethyl, nitro, cyano, carboxyl, carboxylate, alkoxycarbonyl and $NE^1E^2$, where $E^1$ and $E^2$ may be identical or different and are each alkyl, cycloalkyl or aryl, $X^2$ and $X^3$ are, independently of one another, a heterocycle as defined for $X^1$ which is substituted by B, B is either a carbon-carbon single bond or a divalent bridging group, or salts or mixtures thereof.

For the purposes of the present invention, the expression "alkyl" includes both straight-chain and branched alkyl groups. Preferred alkyl groups are straight-chain or branched $C_1$–$C_8$-alkyl groups, preferably $C_1$–$C_6$-alkyl groups and particularly preferably $C_1$–$C_4$-alkyl groups. Examples of alkyl groups are, in particular, methyl, ethyl, propyl, isopropyl, n-butyl, 2-butyl, sec-butyl, tert-butyl, n-pentyl, 2-pentyl, 2-methylbutyl, 3-methylbutyl, 1,2-dimethylpropyl, 1,1-dimethylpropyl, 2,2-dimethylpropyl, 1-ethylpropyl, n-hexyl, 2-hexyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 2-heptyl, 3-heptyl, 2-ethylpentyl, 1-propylbutyl, octyl.

The cycloalkyl group is preferably a $C_5$–$C_7$-cycloalkyl group such as cyclopentyl, cyclohexyl or cycloheptyl.

If the cycloalkyl group is substituted, it preferably bears 1, 2, 3, 4 or 5 substituents, in particular 1, 2 or 3 substituents, selected from among alkyl, alkoxy and halogen.

Aryl is preferably phenyl, tolyl, xylyl, mesityl, naphthyl, anthracenyl, phenanthrenyl, naphthacenyl and in particular phenyl or naphthyl.

Substituted aryl radicals preferably have 1, 2, 3, 4 or 5 substituents, in particular 1, 2 or 3 substituents, selected from among alkyl, alkoxy, carboxyl, carboxylate, trifluoromethyl, nitro, cyano and halogen.

Hetaryl is preferably pyridyl, quinolinyl, acridinyl, pyridazinyl, pyrimidinyl or pyrazinyl.

Substituted hetaryl radicals preferably bear, 1, 2 or 3 substituents selected from among alkyl, alkoxy, trifluoromethyl and halogen.

The above details regarding alkyl, cycloalkyl and aryl radicals apply analogously to alkoxy, cycloalkoxy and aryloxy radicals.

The radicals $NE^1E^2$ are preferably N,N-dimethyl, N,N-diethyl, N,N-dipropyl, N,N-diisopropyl, N,N-di-n-butyl, N,N-di-t-butyl, N,N-dicyclohexyl or N,N-diphenyl.

Halogen is fluorine, chlorine, bromine or iodine, preferably fluorine, chlorine or bromine.

For the purposes of the present invention, carboxylate is preferably a derivative of a carboxylic acid function, in particular a metal carboxylate, a carboxylic ester function or a carboxamide function, particularly preferably a carboxylic ester function. This includes, for example, esters of $C_1$–$C_4$-alkanols such as methanol, ethanol, n-propanol, isopropanol, n-butanol, sec-butanol and tert-butanol.

The radicals $A^1$ in the formulae I.1 and I.2 and the radicals $A^2$ and $A^3$ in the formula I.3, in each case together with the phosphorus atom and the oxygen atom of the phosphinamidite group to which they are bound, preferably form a 5- to 8-membered heterocycle to which one or two aryl and/or hetaryl groups may be fused.

The fused-on aryls of the radicals $A^1$, $A^2$ and/or $A^3$ are preferably benzene or naphthalene, in particular benzene.

The fused-on aryls and/or hetaryls of the radicals $A^1$, $A^2$ and/or $A^3$ are preferably unsubstituted or each have 1, 2 or 3 substituents, in particular 1 or 2 substituents, which are selected from among alkyl, alkoxy, trifluoromethyl, halogen, nitro, cyano, carboxyl and carboxylate.

$A^1$ is preferably a 2,2'-biphenylene, 2,2'-binaphthylene or 2,3-xylylene radical which may bear 1, 2 or 3 subtituents selected from among alkyl, alkoxy, trifluoromethyl, carboxylate or halogen. Here, alkyl is preferably $C_1$–$C_4$-alkyl and in particular t-butyl. Alkoxy is preferably $C_1$–$C_4$-alkoxy and in particular methoxy. Halogen is in particular fluorine, chlorine or bromine.

Radicals $A^2$ and $A^3$ are preferably each a 2,2'-biphenylene radical. The radicals $A^2$ and $A^3$ preferably bear the bridging group B in the para position relative to the phosphorus atom or the oxygen atom of the phosphinamidite group.

The radicals $X^1$ in the formulae I.1 and I.3 and the radicals $X^2$ and $X^3$ in the formula I.2 are preferably each a 5- or 6-membered heterocycle containing at least one nitrogen atom which is bound directly to the phosphorus atom to form a phosphinamidite group. Preferred radicals $X^1$, $X^2$ and/or $X^3$ can additionally contain one or two hetero atom(s) selected from among N, O and S. The additional heteroatoms are preferably nitrogen atoms. Preferred radicals $X^1$, $X^2$ and/or $X^3$ additionally have one or two aryl and/or hetaryl groups fused onto them. Unfused heterocycles are preferably unsubstituted or may bear one, two or three substituents selected from among alkyl, cycloalkyl, aryl, alkoxy, cycloalkoxy, aryloxy, acyl, halogen, trifluoromethyl, nitro, cyano, carboxyl, carboxylate, alkoxycarbonyl and $NE^1E^2$, where $E^1$ and $E^2$ may be identical or different and are alkyl, cycloalkyl or aryl. In the case of singly fused radicals $X^1$, $X^2$ and/or $X^3$ the heterocycle is preferably unsubstituted or has one of the abovementioned substituents on the heterocycle. In the case of singly fused and doubly fused radicals $X^1$, $X^2$ and/or $X^3$, the fused-on rings preferably each have, independently of one another, 1, 2 or 3, in particular 1 or 2, of the abovementioned substituents.

The radicals $X^1$, $X^2$ and $X^3$ are preferably selected from among aromatic heterocycles.

If the radicals $X^1$, $X^2$ and/or $X^3$ bear fused-on aryls, the latter are preferably benzene of naphthalene, in particular benzene.

The radicals $X^1$, $X^2$ and $X^3$ are preferably selected, independently of one another, from among 1-pyrrolyl, 1-pyrazolyl, 1-imidazolyl, 1-triazolyl, 1-indyl, 1-indazolyl, 7-purinyl, 2-isoindyl and 9-carbazolyl which may each bear one, two or three of the abovementioned substituents.

The radicals $X^2$ and $X^3$ are preferably each a 1-pyrrolyl radical which has the bridging group B in the 2 position or in the 3 position, in particular in the 2 position. In addition, it may bear one, two or three of the abovementioned substituents in the 3, 4 and/or 5 position.

The bridging group B is preferably a carbon-carbon single bond or a divalent bridging group having from 1 to 15 atoms in the chain between the flanking compounds.

B is preferably a bridging group of the formula —D—, —(CO)—D—(CO)— or —(CO)—(CO)—, in which
D is a $C_1$–$C_{10}$-alkylene bridge which may have one, two, three or four double bonds and/or bear one, two, three or four substituents selected from among alkyl, alkoxy, halogen, nitro, cyano, carboxyl, carboxylate, cycloalkyl and aryl, where the aryl substituent may additionally bear one, two or three substituents selected from among alkyl, alkoxy, halogen, trifluoromethyl, nitro, alkoxycarbonyl or cyano, and/or the alkylene bridge D may be interrupted by one, two or three nonadjacent, substituted or unsubstituted heteroatoms, and/or the alkylene bridge D may have one, two or three aryl and/or hetaryl groups fused onto it, where the fused-on aryl and hetaryl groups may each bear one, two or three substituents selected from among alkyl, cycloalkyl, aryl, alkoxy, cycloalkoxy, aryloxy, acyl, halogen, trifluoromethyl, nitro, cyano, carboxyl, alkoxycarbonyl and $NE^1E^2$, where $E^1$ and $E^2$ may be identical or different and are each alkyl, cycloalkyl or aryl.

The radical D is preferably a $C_1$–$C_8$-alkylene bridge which, depending on the number of carbon atoms, has 1, 2 or 3 aryl groups fused onto it and/or may bear 1, 2, 3 or 4 substituents selected from among alkyl, cycloalkyl and substituted or unsubstituted aryl, and/or may additionally be interrupted by 1, 2 or 3 substituted or unsubstituted heteroatoms.

The fused-on aryls of the radical D are preferably benzene or naphthalene, in particular benzene. Fused-on benzene rings are preferably unsubstituted or have 1, 2 or 3, in particular 1 or 2, substituents selected from among alkyl, alkoxy, halogen, trifluoromethyl, nitro, carboxyl, alkoxycarbonyl and cyano. Fused-on naphthalenes are preferably unsubstituted or bear, in the ring which is not fused on and/or in the fused-on ring, in each case 1, 2 or 3, in particular 1 or 2, of the substituents mentioned above for the fused-on benzene rings. These are then preferably alkyl or alkoxycarbonyl. In the case of the substituents of the fused-on aryls, alkyl is preferably $C_1$–$C_4$-alkyl and in particular methyl, isopropyl and tert-butyl. Alkoxy is preferably $C_1$–$C_4$-alkoxy and in particular methoxy. Alkoxycarbonyl is preferably $C_1$–$C_4$-alkoxycarbonyl. Halogen is in particular fluorine or chlorine.

If the alkylene bridge of the radical D is interrupted by 1, 2 or 3 substituted or unsubstituted heteroatoms, these are preferably selected from among O, S and $NR^{10}$, where $R^{10}$ is alkyl, cycloalkyl or aryl.

If the alkylene bridge of the radical D is substituted, it bears 1, 2, 3 or 4 substituents which is/are preferably selected from among alkyl, cycloalkyl and aryl, where the aryl substituent may additionally bear 1, 2 or 3 substituents selected from among alkyl, alkoxy, halogen, trifluoromethyl, nitro, alkoxycarbonyl and cyano. The substituents of the alkylene bridge D are preferably selected from among methyl, ethyl, n-propyl, isopropyl, n-butyl, sec-butyl, tert-butyl, phenyl, P-($C_1$–$C_4$-alkyl)phenyl, preferably p-methylphenyl, p-($C_1$–$C_4$-alkoxy)phenyl, preferably p-methoxyphenyl, p-halophenyl, preferably p-chlorophenyl and p-trifluoromethylphenyl.

In a preferred embodiment, D is an unfused $C_1$–$C_7$-alkylene bridge which is substituted and/or interrupted by substituted or unsubstituted heteroatoms, as described above. In particular, the radical D is a $C_1$–$C_5$-alkylene bridge bearing 1, 2, 3 or 4 substituents selected from among methyl, ethyl, n-propyl, isopropyl, n-butyl, sec-butyl, tert-butyl and phenyl.

In a further, preferred embodiment, D is a radical of the formula II.1, II.2, II.3, II,4 or II.5

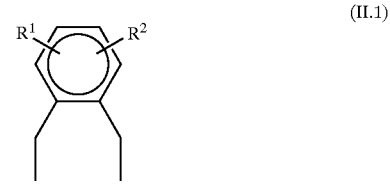
(II.1)

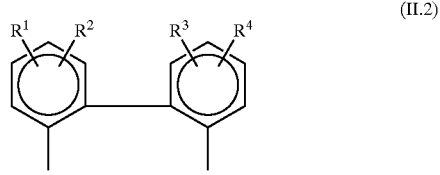
(II.2)

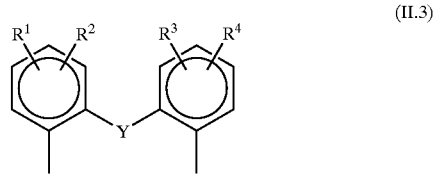
(II.3)

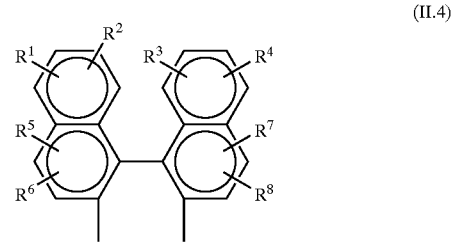
(II.4)

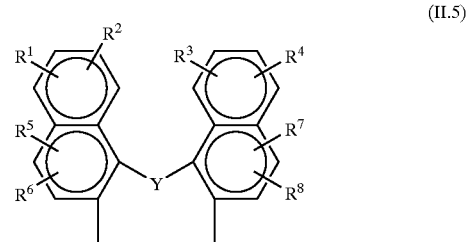
(II.5)

where

Y is O, S, $NR^9$, where
$R^9$ is alkyl, cycloalkyl or aryl, or Y is a $C_1$–$C_3$-alkylene bridge which may have a double bond and/or an alkyl, cycloalkyl- or aryl substituent, where the aryl substituent may bear one, two or three substituents selected from among alkyl, alkoxy, halogen, trifluoromethyl, nitro, alkoxycarbonyl and cyano, or Y is a $C_2$–$C_3$-alkylene bridge which is interrupted by O, S or $NR^9$, $R^1$, $R^2$, $R^3$, $R^4$, $R^5$, $R^6$, $R^7$ and $R^8$ are, independently of one another hydrogen, alkyl, cycloalkyl, aryl, alkoxy, halogen, trifluoromethyl, nitro, alkoxycarbonyl or cyano.

In particular, the phosphinamidite ligand is selected from among the ligands of the formulae IIIa to IIIi

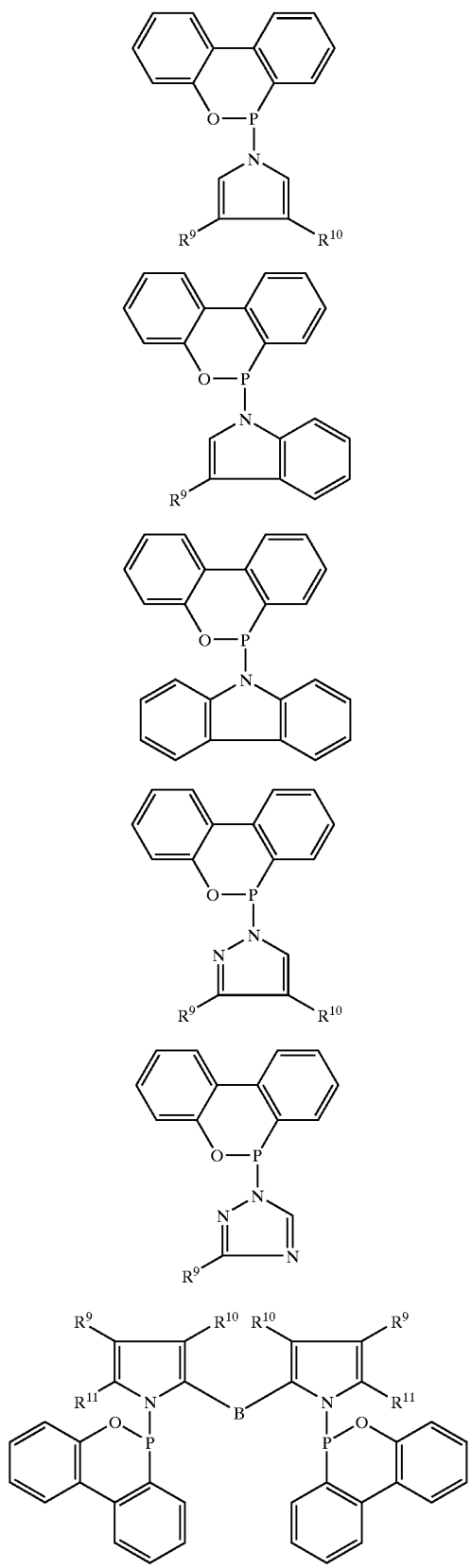

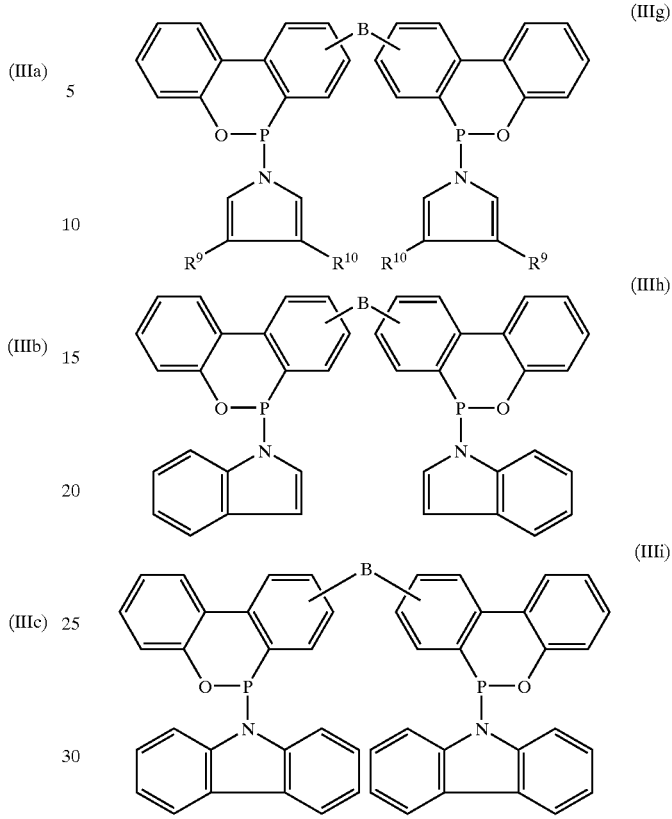

where
R⁹ and R¹⁰ are, independently of one another, hydrogen, methyl, ethyl or trifluoromethyl,
R¹¹ is hydrogen or $COOC_2H_5$,
B is $CH_2$, $C(CH_3)_2$, (CO)—(CO) or (CO)—D—(CO),
  where B in the formulae IIIg, IIIh and IIIi can in each case be bound in the o,o positions, m,m positions or p,p positions relative to the phosphorus atoms and
D is a $C_1$–$C_{10}$-alkylene bridge which may have one, two, three or four double bonds and/or be substituted and/or interrupted by substituted or unsubstituted heteroatoms as described above and/or have aryl and/or hetaryl groups fused onto it.

The catalysts of the present invention may have one or more phosphonamidite ligands of the formulae I.1, I.2 and I.3. In addition to the above-described ligands of the formulae I.1, I.2 and I.3 they may also bear at least one further ligand selected from among halides, amines, carboxylates, acetylacetonate, arylsulfonates or alkylsulfonates, hydride, CO, olefins, dienes, cycloolefins, nitrites, N-containing heterocycles, aromatics and heteraromatics, ethers, $PF_3$ and monodentate, bidentate and multidentate phosphine, phosphinite, phosphonite and phosphite ligands. These further ligands can likewise be monodentate, bidentate or multidentate and coordinate to the metal atom of the catalyst complex. Suitable further phosphorus-containing ligands are, for example, customary phosphine, phosphonite and phosphite ligands.

The phosphinamidite ligands of the formula I.1 used according to the present invention can be prepared, for example, by reacting a hydroxyl group-containing compound of the formula IV with a phosphorus trihalide, preferably $PCl_3$, to give a compound of the formula V and then reacting this with a compound HX¹ containing at least one secondary amino group, as shown in the following scheme

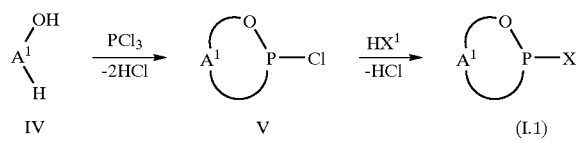

where A¹ and X¹ are as defined above.

Examples of suitable compounds of the formula IV are biphenyl-2-ol, binaphthyl-2-ol, 1,1'-biphenyl-4-phenyl-2-ol, 1,1'-biphenyl-3,3',5,5'-tetra-t-butyl-2-ol, 1,1'-biphenyl-3,3'-di-t-amyl-5,5'-dimethoxy-2-ol, 1,1'-biphenyl-3,3'-di-t-butyl-5,5'-dimethoxy-2-ol, 1,1'-biphenyl-3,3'-di-t-butyl-2-ol, 1,1'-biphenyl-3,3'-di-t-butyl-6,6'-dimethyl-2-ol, 1,1'-biphenyl-3,3',5,5'-tetra-t-butyl-6,6'-dimethyl-2-ol, 1,1'-biphenyl-3,3'-di-t-butyl-5,5'-di-t-butoxy-2-ol, 1,1'-biphenyl-3,3'-di-t-hexyl-5,5'-dimethoxy-2-ol, 1,1'-biphenyl-3-t-butyl-5,5'-dimethoxy-2-ol, 1,1'-biphenyl-3,3'-di[2-(1,3-dioxacyclohexane)]-5,5'-dimethoxy-2-ol, 1,1'-biphenyl-3,3'-diformyl-5,5'-dimethoxy-2-ol and 1,1'-biphenanthren-2-ol, in particular biphenyl-2-ol and binaphthyl-2-ol.

Examples of suitable compounds HX¹ are pyrrole, pyrazole, imidazole, 1-triazole, indole, indazole, purine, isoindole and carbazole.

The phosphinamidite ligands of the formula I.2 used according to the present invention can be prepared, for example, by reacting two mol of at least one compound of the formula V with one mol of a compound HX²—B—X³H, where X², X³ and B are as defined above and the compound contains at least two secondary amino groups, as shown in the following scheme

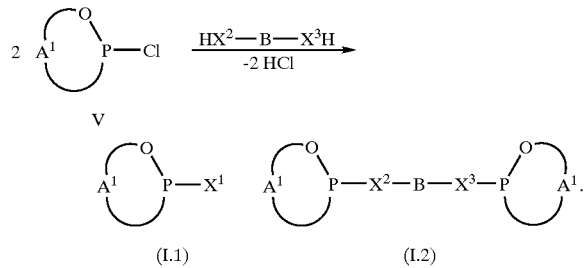

When using only one compound of the formula V, this reaction gives phosphinamidite ligands having two identical phosphinamidite groups. However, if desired, two different compounds of the formula V can also be bridged by a compound HX²—B—X³H. Suitable amines of the formula HX²—B—X³H are, for example, customary alkylene-bridged bispyrroles and diacyl-bridged bispyrroles known to those skilled in the art.

A method of preparing these ligands is described in DE-A-195 21 340, U.S. Pat. No. 5,739,372 and in Phosphorus and Sulfur, 1987, Vol. 31, p. 71 ff for the formation of 6H-dibenz[c,e][1,2]oxaphosphorin ring systems. These documents are hereby fully incorporated by reference.

The phosphinamidite ligands of the formula I.3 used according to the present invention can be prepared, for example, by reacting a compound of the formula VI containing two hydroxyl groups with a phosphorus trihalide, preferably PCl₃, to give a compound of the formula VII and then reacting this with at least one compound HX¹, as described above for the preparation of the phosphinamidite ligands of the formula I.1, as shown in the following scheme

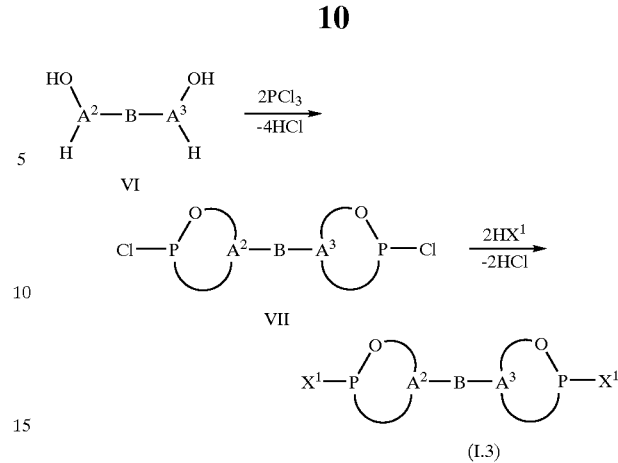

where A², A³ and X¹ are as defined above. If desired, two different compounds HX¹ can also be used for preparing the compounds of the formula I.3.

The compounds of the formulae V and VII may, if desired, be isolated and purified by known methods, e.g. distillation, crystallization, chromatography and the like.

The reaction of compounds of the formula IV to form compounds of the formula V and of compounds of the formula VI to form compounds of the formula VII generally proceeds at an elevated temperature in the range from about 40 to about 200° C.; the reaction can also be carried out with a gradual increase in temperature. In addition, a Lewis acid such as zinc chloride or aluminum chloride can be added as catalyst at the beginning of the reaction or after a certain reaction time. The further reaction of compounds of the formulae V and VII to give the phosphinamidite ligands of the formulae I.1, I.2 and I.3 used according to the present invention is generally carried out in the presence of a base, e.g. an aliphatic amine such as diethylamine, dipropylamine, dibutylamine, trimethylamine, tripropylamine and preferably triethylamine or pyridine. The preparation can also be carried out by deprotonation of the nitrogen heterocycle using a base and subsequent reaction with a compound of the formula V or VII. Bases suitable for the deprotonation are, for example, alkali metal hydrides, preferably sodium hydride and potassium hydride, alkali metal amides, preferably sodium amide, lithium diisopropylamide, n-butyllithium, etc.

The preparation of the phosphinamidite ligands used according to the present invention advantageously proceeds without use of organomagnesium or organolithium compounds. The simple reaction sequence allows wide variation of the ligands. The preparation can thus be carried out efficiently and economically from readily available starting materials.

In general, the catalysts or catalyst precursors used in each case form catalytically active species of the formula $H_xM_y(CO)_zL_q$, where M is a metal of transition group VIII, L is a phosphinamidite ligand used according to the present invention and q, x, y, z are integers which depend on the valence and type of metal and on the number of co-ordination positions occupied by the ligand L, under hydroformylation conditions. Preferably, z and q are, independently of one another, at least 1, e.g. 1, 2 or 3. The sum of z and q is preferably from 2 to 5. The complexes can, if desired, additionally contain at least one of the above-described further ligands.

The metal M is preferably cobalt, ruthenium, rhodium, nickel, palladium, platinum, osmium or iridium, in particular cobalt, ruthenium, iridium, rhodium, nickel, palladium or platinum.

In a preferred embodiment, the hydroformylation catalysts are prepared in situ in the reactor used for the hydroformylation reaction. However, the catalysts of the present invention can, if desired, also be prepared separately and isolated by customary methods. For the in-situ preparation of the catalysts of the present invention, it is possible, for example, to react at least one phosphinamidite ligand of the formulae I.1, I.2 and/or I.3, a compound or a complex of a metal of transition group VIII, if desired at least one further additional ligand and, if desired, an activator in an inert solvent under the hydroformylation conditions.

Suitable rhodium compounds or complexes are, for example, rhodium(II) and rhodium(III) salts such as rhodium(III) chloride, rhodium(III) nitrate, rhodium(III) sulfate, potassium rhodium sulfate, rhodium(II) or rhodium (III) carboxylate, rhodium(II) and rhodium(III) acetate, rhodium(III) oxide, salts of rhodic(III) acid, trisammonium hexachlororhodate(III) etc. Also suitable are rhodium complexes such as biscarbonyl rhodium acetylacetonate, acetylactonatobisethylenerhodium(I) etc. Preference is given to using biscarbonyl rhodium acetylacetonate or rhodium acetate.

Ruthenium salts or compounds are likewise suitable. Suitable ruthenium salts are, for example, ruthenium(III) chloride, ruthenium(IV), ruthenium(VI) or ruthenium(VIII) oxide, alkali metal salts of oxo acids of ruthenium, e.g. $K_2RuO_4$ or $KRuO_4$ or complexes such as $RuHCl(CO)(PPh_3)_3$. It is also possible to use metal carbonyls of ruthenium such as dodecacarbonyltriruthenium or octadecacarbonylhexaruthenium, or mixed forms in which CO is partially replaced by ligands of the formula $PR_3$, e.g. $Ru(CO)_3(PPh_3)_2$, in the process of the present invention.

Examples of suitable cobalt compounds are cobalt(II) chloride, cobalt(II) sulfate, cobalt(II) carbonate, cobalt(II) nitrate, their amine or hydrate complexes, cobalt carboxylates such as cobalt acetate, cobalt ethylhexanoate, cobalt naphthanoate, and also the cobalt caprolactamate complexes. Here too, the carbonyl complexes of cobalt, e.g. octacarbonyldicobalt, dodecacarbonyltetracobalt and hexadecacarbonylhexacobalt, can be used.

The abovementioned and further suitable compounds of cobalt, rhodium, ruthenium and iridium are known in principle and are adequately described in the literature, or they can be prepared by a person skilled in the art using methods analogous to those for the known compounds.

Suitable activators are, for example, Brönsted acids, Lewis acids, such as $BF_3$, $AlCl_3$, $ZnCl_2$, and Lewis bases.

As solvent, preference is given to using the aldehydes which are formed in the hydroformylation of the respective olefins and also their higher-boiling downstream reaction products, e.g. the products of the aldolcondensation. Further solvents which are likewise suitable are aromatics such as toluene and xylenes, hydrocarbons or mixtures of hydrocarbons, including for dilution of the abovementioned aldehydes and the downstream products of the aldehydes. In the case of sufficiently hydrophilic ligands, it is also possible to use water, alcohols such as methanol, ethanol, n-propanol, isopropanol, n-butanol, isobutanol, ketones, such as acetone and methyl ethyl ketone etc.

The molar ratio of phosphinamidite ligand to metal of transition group VIII is generally in a range from about 1:1 to 1,000:1.

The present invention further provides a process for the hydroformylation of compounds containing at least one ethylenically unsaturated double bond by reaction with carbon monoxide and hydrogen in the presence of at least one of the hydroformylation catalysts of the present invention.

Suitable substrates for the hydroformylation process of the present invention are, in principle, all compounds which contain one or more ethylenically unsaturated double bonds. These include, for example, olefins such as α-olefins, internal straight-chain and internal branched olefines. Suitable α-olefins are, for example, ethylene, propene, 1-butene, 1-pentene, 1-hexene, 1-heptene, 1-octene, 1-nonene, 1-decene, 1-undecene, 1-dodecene, etc.

Preferred straight-chain internal olefins are $C_4$–$C_{20}$-olefins, such as 2-butene, 2-pentene, 2-hexene, 3-hexene, 2-heptene, 3-heptene, 2-octene, 3-octene, 4-octene, etc.

Preferred branched, internal olefins are $C_4$–$C_{20}$-olefins such as 2-methyl-2-butene, 2-methyl-2-pentene, 3-methyl-2-pentene, branched, internal heptene mixtures, branched, internal octene mixtures, branched, internal nonene mixtures, branched, internal dodecene mixtures, branched, internal undecene mixtures, branched, internal dodecene mixtures, etc.

Further suitable olefins for the hydroformylation reaction are $C_5$–$C_8$-cycloalkenes, such as cyclopentene, cyclohexene, cycloheptene, cyclooctene and their derivatives, for example, their $C_1$–$C_{20}$-alkyl derivatives having from 1 to 5 alkyl substituents. Additional olefins which are suitable for the hydroformylation reaction are vinylaromatics such as styrene, α-methylstyrene, 4-isobutylstyrene, etc. Other olefins which are suitable for the hydroformylation reaction are α,β-ethylenically unsaturated monocarboxylic and/or dicarboxylic acids, their esters, monoesters and amides, for example acrylic acid, methacrylic acid, maleic acid, fumaric acid, crotonic acid, itaconic acid, methyl 3-pentenoate, methyl 4-pentenoate, methyl oleate, methyl acrylate, methyl methacrylate, and saturated nitriles such as 3-pentenenitrile, 4-pentenenitrile, acrylonitrile, vinyl ethers such as vinyl methyl ether, vinyl ethyl ether, vinyl propyl ether, etc. $C_1$–$C_{20}$-alkenols, -alkenediols and -alkadienols such as 2,7-octadien-1-ol. Further suitable substrates are dienes or polyenes having isolated or conjugated double bonds. These include, for example, 1,3-butadiene, 1,4-pentadiene, 1,5-hexadiene, 1,6-heptadiene, 1,7-octadiene, vinylcyclohexene, dicyclopentadiene, 1,5,9-cyclooctatriene and homopolymers and copolymers of butadiene.

Preference is given to a process in which the hydroformylation catalyst is prepared in situ by reacting at least one phosphinamidite ligand as is used according to the present invention, a compound or a complex of a metal of transition group VIII and, if desired, an activator in an inert solvent under the hydroformylation conditions.

The hydroformylation reaction can be carried out continuously, semicontinuously or batchwise.

Suitable reactors for the continuous reaction are known to those skilled in the art and are described, for example, in Ullmanns Enzyklopädie der technischen Chemie, Vol. 1, 3. 3rd Edition, 1951, p. 743 ff.

Suitable pressure-rated reactors are likewise known to those skilled in the art and are described, for example, in Ullmanns Enzyklopädie der technischen Chemie, Vol. 1, 3. 3rd Edition, 1951, p. 769 ff. In general, the process of the present invention is carried out using an autoclave which may, if desired, be provided with a stirring apparatus and an interior lining.

The composition of the synthesis gas (carbon monoxide and hydrogen) used in the process of the present invention can vary within wide limits. The molar ratio of carbon monoxide and hydrogen is generally from about 5:95 to 70:30, preferably from about 40:60 to 60:40. Particular preference is given to using a molar ratio of carbon monoxide and hydrogen in the region of about 1:1.

The temperature of the hydroformylation reaction is generally in a range from about 20 to 180 °C., preferably from about 50 to 150° C. The reaction is generally carried out at the partial pressure of the reaction gas at the reaction temperature selected. In general, the pressure is in a range from about 1 to 700 bar, preferably from 1 to 600 bar, in particular from 1 to 300 bar. The reaction pressure can be varied as a function of the activity of the novel hydroformylation catalyst used. In general, the novel catalysts based on phosphinamidite ligands allow a reaction in a low pressure range, for example in a range from 1 to 100 bar.

The hydroformylation catalysts of the present invention can be separated from the reaction product of the hydroformylation reaction by customary methods known to those skilled in the art and can generally be reused for the hydroformylation.

The catalysts of the present invention advantageously display a high activity, so that the corresponding aldehydes are generally obtained in good yields. In the hydroformylation of α-olefins and of internal, linear olefins, they additionally display a very low selectivity to the hydrogenation product of the olefin used.

The above-described, novel catalysts which comprise chiral phosphinamidite ligands are suitable for enantioselective hydroformylation.

The present invention further provides for the use of catalysts comprising one of the above-described phosphinamidite ligands for the hydroformylation of compounds having at least one ethylenically unsaturated double bond.

A further field of application for the catalysts of the present invention is the hydrocyanation of olefins. The hydrocyanation catalysts of the present invention also comprise complexes of a metal of transition group VIII, in particular cobalt, nickel, ruthenium, rhodium, palladium, platinum, preferably nickel, palladium and platinum and very particularly preferably nickel. In general, the metal is present in zero-valent form in the metal complex of the present invention. The preparation of the metal complexes can be carried out as described above for use as hydroformylation catalysts. The same applies to the in-situ preparation of the hydrocyanation catalysts of the present invention.

A nickel complex suitable for preparing a hydrocyanation catalyst is, for example, bis(1,5-cyclooctadiene)nickel(0).

If desired, the hydrocyanation catalysts can be prepared in situ using a method analogous to that described for the hydroformylation catalysts.

The present invention therefore also provides a process for preparing nitrites by catalytic hydrocynation in which the hydrocyanation is carried out in the presence of at least one of the above-described catalysts of the present invention. Suitable olefins for the hydrocyanation are generally the olefins mentioned above as starting materials for the hydroformylation. A specific embodiment of the process of the present invention relates to the preparation of mixtures of monoolefinic $C_5$-mononitriles having nonconjugated C=C— and C≡N bonds by catalytic hydrocyanation of 1,3-butadiene or 1,3-butadiene-containing hydrocarbon mixtures and isomerization/further reaction to form saturated $C_4$-dinitriles, preferably adiponitrile, in the presence of at least one catalyst according to the present invention. When using hydrocarbon mixtures for preparing monoolefinic $C_5$-mononitriles by the process of the present invention, preference is given to using a hydrocarbon mixture which has a 1,3-butadiene content of at least 10% by volume, preferably at least 25% by volume, in particular at least 40% by volume.

1,3-butadiene-containing hydrocarbon mixtures are obtainable on an industrial scale. Thus, for example, the refining of petroleum by steam cracking of naphtha produces a hydrocarbon mixture, known as $C_4$ fraction, where about 40% is 1,3-butadiene and the remainder is monoolefins and multiply unsaturated hydrocarbons together with alkanes. These streams always also contain small amounts of generally up to 5% of alkynes, 1,2-dienes and vinylacetylene.

Pure 1,3-butadiene can be isolated from industrially available hydrocarbon mixtures by, for example, extractive distillation.

The catalysts of the present invention can be advantageously used for the hydrocyanation of such olefin-containing, in particular 1,3-butadiene-containing, hydrocarbon mixtures, generally even without prior purification of the hydrocarbon mixture by distillation. Any olefins present which impair the effectiveness of the catalysts, e.g. alkynes or cumulenes, can, if necessary be removed from the hydrocarbon mixture by selective hydrogenation prior to the hydrocyanation. Suitable processes for selective hydrogenation are known to those skilled in the art.

The hydrocyanation of the present invention can be carried out continuously, semicontinuously or batchwise. Suitable reactors for the continuous reaction are known to those skilled in the art and are described, for example, in Ullmanns Enzyklopädie der technischen Chemie, Vol. 1, 3rd Edition, 1951, p. 743 ff. The continuous variant of the process of the invention is preferably carried out using a cascade of stirred tanks or a tube reactor. Suitable reactors, which may be pressure rated, for the semicontinuous or continuous process are known to those skilled in the art and are described, for example, in Ullmanns Enzyklopädie der technischen Chemie, Vol. 1, 3rd Edition, 1951, p. 769 ff. The process of the present invention is generally carried out using an autoclave which may, if desired, be provided with a stirring apparatus and an interior lining.

The hydrocyanation catalysts can be separated from the reaction product of the hydrocyanation reaction by customary methods known to those skilled in the art and can generally be reused for the hydrocyanation.

The invention is illustrated by the following, non-restrictive examples.

EXAMPLES

The ligands described below can, if desired, be further purified by customary purification methods known to those skilled in the art, for example crystallization and distillation.

A) Preparation of the Ligands IIIa to IIIc

Example 1

Preparation of Ligand IIIa 206 g (1.5 mol) of phosphorus trichloride and 204 g (1.2 mol) of biphenyl-2-ol are, while stirring in an argon atmosphere, slowly heated to 50° C. and then heated further to 140° C. over a period of 8 hours. Vigorous hydrogen chloride evolution occurs and the solution becomes yellow. After cooling to 120° C., a catalytic amount of zinc chloride (1.2 g; 17 mmol) is added and the mixture is heated at 140° C. for 24 hours. On subsequent distillation, the reaction product 6-chloro-(6H)-dibenz[c,e][1,2]oxaphosphorin goes over at a boiling point of 132° C. (0.2 mbar).

Yield: 194.8 g(69%) of white crystals;

$^{31}$P-NMR spectrum: δ (ppm) 134.5.

Further methods of preparing 6-chloro-(6H)-dibenz[c,e][1,2]-oxaphosphorin are described in DE-A-20 34 887 and EP-A-0 582 957.

2.9 g of potassium hydride (35% strength suspension in mineral oil; 25 mmol) and 80 ml of tetrahydrofuran are placed under an argon atmosphere in a reaction vessel. 1.75 g (26 mmol) of pyrrole are then slowly added dropwise, with the temperature rising to about 33° C. After hydrogen evolution has stopped, 6 g (26 mmol) of 6-chloro-(6H)-dibenz[c,e][1,2]oxaphosphorin is added as a solution in 40 ml of tetrahydrofuran and the mixture is subsequently stirred for 12 hours at room temperature. The mixture is evaporated to dryness, taken up in toluene and filtered through a 2 cm kieselguhr column. Evaporation of the solvent gives the ligand IIIa as a white solid.

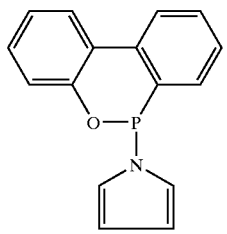

(IIIa)

Yield: 3.3 g (50%) of white crystals;
$^{31}$P-NMR spectrum (CDCl$_3$): δ (ppm) 77.2
$^1$H-NMR spectrum: corresponds to the proposed structure An alternative method of preparing ligand IIIa is to place 9.7 g (36.6 mmol) of 6-chloro-(6H)-dibenz[c,e][1,2]oxaphosphorin as a solution in 80 ml of toluene in a reaction vessel, subsequently to add 4.9 g (73.2 mmol) of pyrrole and then to slowly add 7.6 g (75 mmol) of triethylamine dropwise at room temperature, immediately forming a mist of triethylamine hydrochloride. The mixture is stirred for 6 hours at 70° C. and subsequently for 12 hours at room temperature. After filtration, the resulting filtrate is evaporated to dryness, the residue is taken up in methyl tert-butyl ether and subsequently precipitated by cooling to −30° C.
Yield: 6.7 g (72%);
$^{31}$P-NMR spectrum (CDCl$_3$): as above
$^1$H-NMR spectrum: corresponds to the proposed structure

Example 2
Preparation of Ligand IIIb

The ligand IIIb is prepared using a method analogous to that described in Example 1 by reacting 6-chloro-(6H)-dibenz[c,e][1,2]oxaphosphorin with indol and triethylamine as base. The product obtained is purified by washing with water and recrystallization from acetonitrile.

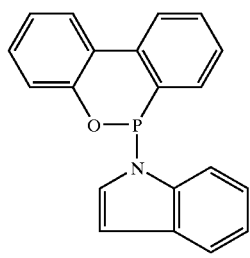

(IIIb)

$^{31}$P-NMR spectrum (CDCl$_3$): δ (ppm) 66.7
$^1$H-NMR spectrum: corresponds to the proposed structure

Example 3
Preparation of Ligand IIIc

The ligand IIIc is prepared using a method analogous to that described in Example 1 by reacting 6-chloro-(6H)-dibenz[c,e][1,2]oxaphosphorin with carbazole and triethylamine as base.

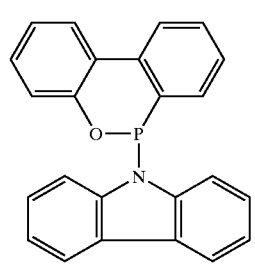

(IIIc)

$^{31}$P-NMR spectrum-(CDCl3): δ (ppm) 81.4
$^1$H-NMR spectrum: corresponds to the proposed structure B) Hydroformylations

Example 4
Hydroformylation of 1-octene

In a 300 ml steel autoclave fitted with sparging stirrer, 123 mg of biscarbonylrhodium acetylacetonate, 680 mg of ligand IIIa, 22.5 g of 1-octene and 25 ml of Texanol® (solvent based on 2,2,4-trimethylpentane-1,3-diol monoisobutyrate) were reacted at 100° C. under a protective argon atmosphere with a synthesis gas mixture of CO/H$_2$ (1:1) at 40 bar (108 ppm of Rh; ligand/metal ratio=54). After a reaction time of 4 hours, the autoclave was vented and emptied. The mixture was analyzed by means of gas chromatography (GC) using an internal standard. The conversion was 100%, the selectivity in respect of the nonanal isomers was 96% and the proportion of n-isomer was 80%.

Example 5
Hydroformylation of 1-octene

The procedure of Example 4 was repeated using 134 mg of biscarbonylrhodium acetylacetonate, 310 mg of ligand IIIb, 22.5 g of 1-octene and 25 ml of Texanol® for the hydroformylation (118 ppm of Rh; ligand/metal ratio=19). The conversion was 99%, the selectivity in respect of nonanal isomers was 88% and the proportion of n-isomer was 68%.

Example 6
Hydroformylation of 1-octene

The procedure of Example 4 was repeated using 12.4 mg of biscarbonylrhodium acetylacetonate, 480 mg of ligand IIIc, 22.5 g of 1-octene and 22.5 g of Texanol® for the hydroformylation (109 ppm of Rh; ligand/metal ratio=45). The conversion was 99%, the selectivity in respect of nonanal isomers was 82% and the proportion of n-isomer was 51%.

Example 7
Hydroformylation of 3-pentene Nitrile

The general procedure of Example 4 was repeated using 6.2 mg of biscarbonylrhodium acetylacetonate, 322 mg of ligand IIIa, 10 g of 3-pentenenitrile and 15 g of xylene at a temperature of 110° C., a pressure of 80 bar and a reaction time of 4 h for the hydroformylation (100 ppm of Rh; ligand/metal ratio=50). The conversion was 69% and the selectivity in respect of 3-formylvaleronitrile was 65%, that in respect of 4-formylvaleronitrile was 24% and that in respect of 5-formylvaleronitrile was 4%.

Example 8
Hydroformylation of 3-pentenenitrile

The general procedure of Example 4 was repeated using 6.2 mg of biscarbonylrhodium acetylacetonate, 382 mg of ligand IIIb, 10 g of 3-pentenenitrile and 15 g of xylene at a temperature of 110° C., a pressure of 70 bar and a reaction time of 4 h for the hydroformylation (100 ppm of Rh; ligand/metal ratio=50). The conversion was 99% and the selectivity in respect of 3-formylvaleronitrile was 59%, that in respect of 4-formylvaleronitrile was 30% and that in respect of 5-formylvaleronitrile was 9%.

Example 9
Hydroformylation of 3-pentenenitrile

The general procedure of Example 4 was repeated using 6.2 mg of biscarbonylrhodium acetylacetonate, 443 mg of ligand IIIc, 10 g of 3-pentenenitrile and 15 g of xylene at a temperature of 110° C., a pressure of 70 bar and a reaction time of 4 h for the hydroformylation (100 ppm of Rh; ligand/metal ratio=50). The conversion was 80% and the selectivity in respect of 3-formylvaleronitrile was 41%, that in respect of 4-formylvaleronitrile was 38% and that in respect of 5-formylvaleronitrile was 18%.

Example 10
Hydroformylation of Octene-N

The general procedure of Example 4 was repeated using 126 mg of biscarbonylrhodium acetylacetonate, 270 mg of ligand IIIa, 22.5 g of octene-N and 22.5 g of Texanol® at a temperature of 130° C., a pressure of 60 bar and a reaction time of 6 h for the hydroformylation (111 ppm of Rh; ligand/metal ratio=20). The conversion was 59% and the selectivity in respect of nonanal isomers was 85% and that in respect of nonanol isomers was 11%.

We claim:

1. A catalyst comprising at least one complex of a metal of transition group VIII comprising at least one monodentate, bidentate or multidentate phosphinamidite ligand of the formulae I.1, I.2 and/or I. 3

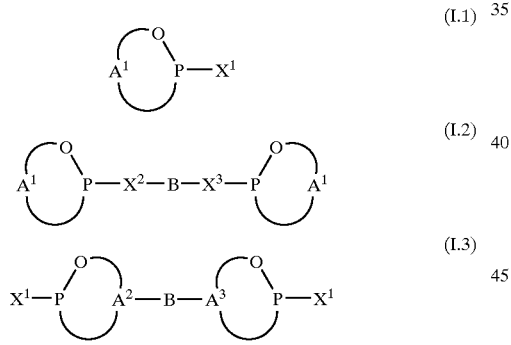

where
$A^1$ represents carbon ring members which, together with the phosphorus atom and the oxygen atom to which it is bound, form a 5- to 8-membered heterocycle which optionally has one, two or three fused-on cycloalkyl, aryl and/or heteroaryl groups, where each of the fused-on groups optionally carries, independently of one another, one, two or three substituents selected from the group consisting of alkyl, alkoxy, halogen, nitro, cyano, carboxyl and carboxylate, $A^2$ and $A^3$ are, independently of one another, carbon ring members which are part of a heterocycle as defined for $A^1$ which is substituted by B, $X^1$ is a 5- to 8-membered heterocycle which contains a nitrogen atom bound directly to the phosphorus atom, where the heterocycle optionally contains one or two additional heteroatom(s) selected from the group consisting of N, O and S, and/or has one, two or three fused-on cycloalkyl, aryl and/or heteroaryl groups, where the heterocycle and/or each of the fused-on groups optionally carries, independently of one another, one, two or three substituents selected from the group consisting of alkyl, cycloalkyl, aryl, alkoxy, cycloalkoxy, aryloxy, acyl, halogen, trifluoromethyl nitro, cyano, carboxyl, carboxylate, alkoxycarbonyl and $NE^1E^2$, where $E^1$ and $E^2$ are identical or different and are each alkyl, cycloalkyl or aryl, $X^2$ and $X^3$ are, independently of one another, a heterocycle as defined for $X^1$ which is substituted by B, B is either a carbon-carbon single bond or a divalent bridging group, or salts or mixtures thereof.

2. A catalyst as claimed in claim 1, wherein B is a bridging group of the formula —D—, —(CO)—D—(CO)— or —(CO)—(CO)—, in which D is a $C_1$–$C_{10}$-alkylene bridge which optionally has one, two, three or four double bonds and/or carries one, two, three or four substituents selected from the group consisting of alkyl, alkoxy, halogen, nitro, cyano, carboxyl, carboxylate, cycloalkyl and aryl, where the aryl substituent in turn optionally carries one, two or three substituents selected from the group consisting of alkyl, alkoxy, halogen, trifluoromethyl, nitro, alkoxycarbonyl and cyano, and/or the alkylene bridge D is optionally interrupted by one, two or three nonadjacent, substituted or unsubstituted heteroatoms, and/or the alkylene bridge D optionally has one, two or three fused-on aryl and/or heteroaryl groups, where the fused-on aryl and heteroaryl groups optionally carry one, two or three substituents selected from the group consisting of alkyl, cycloalkyl, aryl, alkoxy, cycloalkoxy, aryloxy, aryl, halogen, trifluoromethyl, nitro, cyano, carboxyl, alkoxycarbonyl and $NE^1E^2$, where $E^1$ and $E^2$ are identical or different and are each alkyl, cycloalkyl or aryl.

3. A catalyst as claimed in claim 2, wherein D is a radical of the formula II.1, II.2, II.3, II.4, or II.5

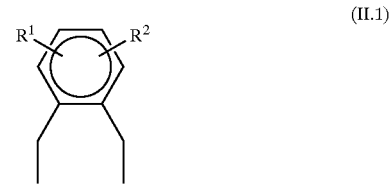

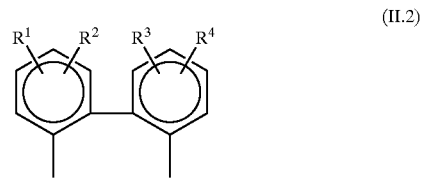

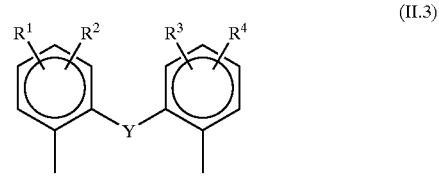

(II.4)

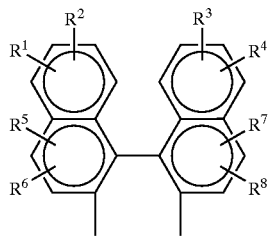

(II.5)

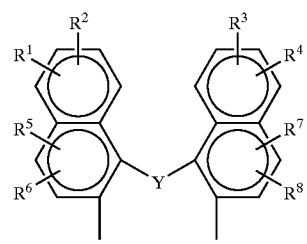

where

- Y is O, or NR⁹, where R⁹ is alkyl, cycloalkyl or aryl,
- or Y is a $C_1$–$C_3$-alkylene bridge which optionally has a double bond and/or an alkyl, cycloalkyl or aryl substituent, where the aryl substituent in turn optionally carries one, two or three substituents selected from the group consisting of alkyl, alkoxy, halogen, trifluoromethyl, nitro, alkoxycarbonyl and cyano,
- or Y is a $C_2$–$C_3$-alkylene bridge which is interrupted by O, S or NR⁹,
- R¹, R², R³, R⁴, R⁵, R⁶, R⁷ and R⁸ are, independently of one another hydrogen, alkyl, cycloalkyl, aryl, alkoxy, halogen, trifluoromethyl, nitro, alkoxycarbonyl or cyano.

4. A catalyst as claimed in claim 1, wherein the phosphinamidite ligand is selected from the group consisting of ligands of the formulae IIIa to IIIi (IIIa)

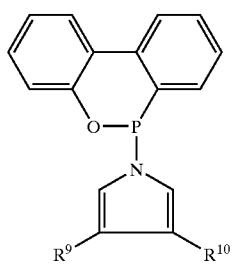

(IIIb)

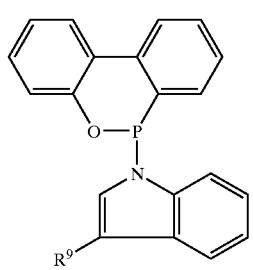

(IIIc)

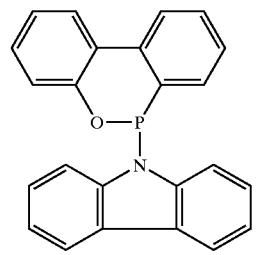

(IIId)

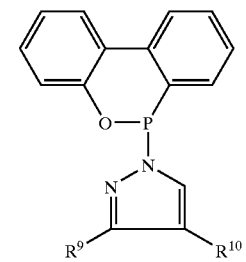

(IIIe)

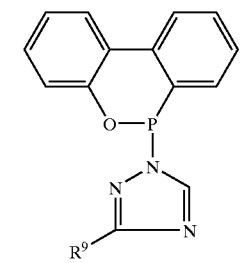

(IIIf)

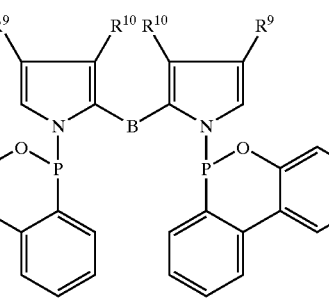

(IIIg)

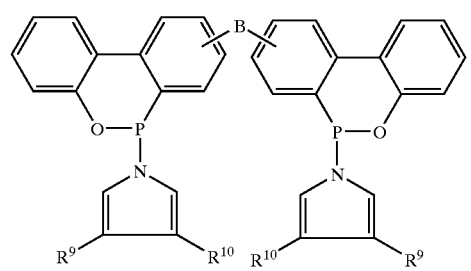

(IIIh)

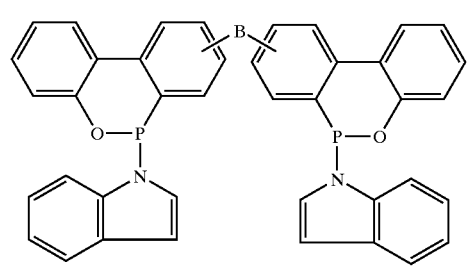

-continued (IIIi)

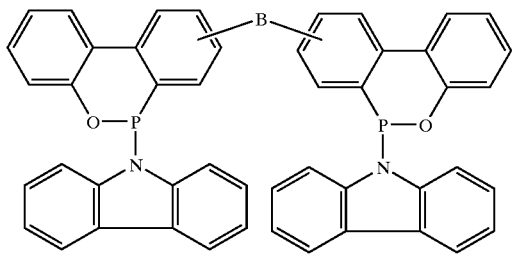

where

R⁹ and R¹⁰ are, independently of one another, hydrogen, methyl, ethyl or trifluoromethyl, R¹¹ is hydrogen or COOC₂H₅, B is CH₂, C(CH₃)₂, (CO)—(CO) or (CO)—D—(CO), where B in the formulae IIIg, IIIh and IIIi is in each case bound to the o,o positions, m,m positions or p,p positions relative to the phosphorus atoms, and D is a C₁–C₁₀-alkylene bridge which optionally has one, two, three or four double bonds and/or carries one, two, three or four substituents selected from the group consisting of alkyl, alkoxy, halogen, nitro, cyano, carboxyl, carboxylate, cycloalkyl and aryl, where the aryl substituent in turn optionally carries one, two or three substituents selected from the group consisting of alkyl, alkoxy, halogen, trifluoromethyl, nitro, alkoxycarbonyl and cyano, and/or the alkylene bridge D is optionally interrupted by one, two or three nonadjacent, substituted or unsubstituted heteroatoms, and/or the alkylene bridge D optionally has one, two or three fused-on aryl and/or heteroaryl groups, where the fused-on aryl and heteroaryl groups optionally carry one, two or three substituents selected from the group consisting of alkyl, cycloalkyl, aryl, alkoxy, cycloalkoxy, aryloxy, aryl, halogen, trifluoromethyl, nitro, cyano, carboxyl, alkoxycarbonyl and NE¹E², where E¹ and E² are identical or different and are each alkyl, cycloalkyl or aryl, or D is a radical of the formula II.1, II.2, II.3, II.4 or II.5

(II.1)

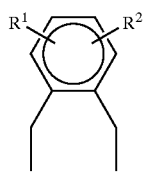

(II.2)

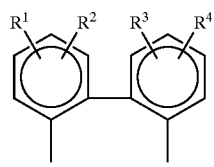

(II.3)

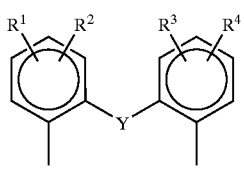

(II.4)

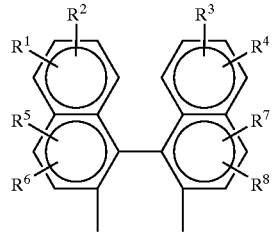

(II.5)

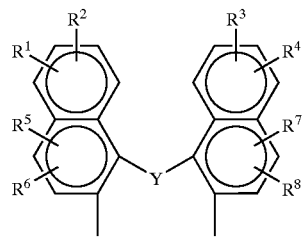

where

Y is O, S or NR⁹, where R⁹ is alkyl, cycloalkyl or aryl, or Y is a C₁–C₃-alkylene bridge which optionally has a double bond and/or an alkyl, cycloalkyl or aryl substituent, where the aryl substituent in turn optionally carries one, two or three substituents selected from the group consisting of alkyl, alkoxy, halogen, trifluoromethyl, nitro, alkoxycarbonyl and cyano, or Y is a C₂–C₃-alkylene bridge which is interrupted by O, S or NR⁹, R¹, R², R³, R⁴, R⁵, R⁶, R⁷ and R8 are, independently of one another hydrogen, alkyl, cycloalkyl, aryl, alkoxy, halogen, trifluoromethyl, nitro, alkoxycarbonyl or cyano.

5. A catalyst as claimed in claim 1, wherein the metal of transition group VIII is selected from the group n consisting of cobalt, ruthenium, iridium, rhodium, nickel, palladium and platinum.

6. A catalyst as claimed in claim 1 which further comprises at least one further ligand selected from the group consisting of halides, amines, carboxylates, acetylacetonate, arylsulfonates or alkylsulfonates, hydride, CO, olefins, dienes, cycloolefins, nitriles, N-containing heterocycles, aromatics and heteroaromatics, ethers, PF₃ and monodentate, bidentate and multidentate phosphine, phosphinite, phosphonite and phosphite ligands.

7. A process for the hydroformylation of compounds which contain at least one ethylenically unsaturated double bond by reaction with carbon monoxide and hydrogen in the presence of a hydroformylation catalyst, wherein the hydroformylation catalyst used is a catalyst as claimed in claim 1.

8. A process for the hydrocyanation of compounds containing at least one ethylenically unsaturated double bond by reaction with hydrogen cyanide in the presence of a hydrocyanation catalyst, wherein the hydrocyanation catalyst used is a catalyst as claimed in claim 1.

9. A process as claimed in claim 7, wherein the hydroformylation catalyst is prepared in situ by reacting at least one phosphinamidite ligand, a compound or a complex of a metal of transition group VIII and optionally an activator in an inert solvent under the hydroformylation conditions.

10. A process as claimed in claim 8, wherein the hydrocyanation catalyst is prepared in situ by reacting at least one phosphinamidite ligand, a compound or a complex of a metal of transition group VIII and optionally an activator in an inert solvent under the hydrocyanation conditions.

* * * * *